US00PP15523P2

(12) United States Plant Patent
Meserve et al.

(10) Patent No.: US PP15,523 P2
(45) Date of Patent: Feb. 1, 2005

(54) ***ILEX×KOEHNEANA* PLANT NAMED 'CONAYULE'**

(50) Latin Name: *Ilex×koehneana*
Varietal Denomination: Conayule

(75) Inventors: Kathleen K. Meserve, deceased, late of Vero Beach, FL (US); by Frederick L. Meserve, Jr., legal representative, Kennett Square, PA (US); by Anne M. Davis, legal representative, Winnetka, IL (US); by Marcia M. Poutiatine, legal representative, Vero Beach, FL (US)

(73) Assignee: CP Delaware, Inc., Wilmington, DE (US)

( * ) Notice: Subject to any disclaimer, the term of this patent is extended or adjusted under 35 U.S.C. 154(b) by 37 days.

(21) Appl. No.: 10/700,482

(22) Filed: Nov. 5, 2003

(Under 37 CFR 1.47)

(51) Int. Cl.[7] ..... A01H 5/00

(52) U.S. Cl. ..... Plt./247

(58) Field of Search ..... Plt./247

*Primary Examiner*—Kent Bell
(74) *Attorney, Agent, or Firm*—Burns, Doane, Swecker & Mathis, L.L.P.

(57) ABSTRACT

A new and distinct *Ilex* cultivar is provided which originated by the crossing of an unnamed and unpatented plant of *Ilex aquifolium* and unnamed and unpatented plant of *Ilex latifolia*. The resulting evergreen plant displays an attractive moderate to fast growing upright moderately narrow pyramidal growth habit. Showy red fruit is formed in abundance that commonly is retained on the plant well into February. Good cold tolerance as well as drought tolerance are exhibited. The plant can be grown to provide attractive ornamentation in the landscape throughout the year as a specimen planting or as a screen or hedge.

7 Drawing Sheets

Botanical/commercial classification: *Ilex×koehneana/Ilex* Plant.
Varietal denomination: cv. 'Conayule'.

SUMMARY OF THE INVENTION

The present invention relates to a new and distinct female cultivar of *Ilex×koehneana* which originated in the course of a planned breeding program that was carried out at St. James, Long Island, N.Y., U.S.A. The female parent (i.e., seed parent) was an unnamed and unpatented plant of *Ilex aquifolium* (i.e., English Holly), and the male parent (i.e., pollen parent) was an unnamed and unpatented plant of *Ilex latifolia* (i.e., Lusterleaf Holly). The objective of the breeding program and selection procedure was to create and discover a new *Ilex* cultivar having improved hardiness, an attractive upright moderately narrow growth habit, a propensity for forming attractive bright red fruit in abundance, and good adaptability to fulfill a wide variety of landscape needs. The parentage of the new cultivar can be summarized as follows:

*Ilex aquifolium×Ilex latifolia.*

A cross of such species commonly is designated *Ilex× koehneana.*

The new plant of the present invention has been evaluated for approximately 30 years in a test planting at West Grove, Pa., U.S.A.

It was found that the new and distinct *Ilex×koehneana* plant of the present invention is readily distinguishable from previously known *Ilex* cultivars and exhibits the following combination of characteristics:

(a) displays an attractive moderate to fast growing upright moderately narrow pyramidal growth habit,
(b) forms in abundance showy red fruit that commonly is retained on the plant well into February,
(c) displays improved cold hardiness, and
(d) displays good drought tolerance in established plantings.

A 30 year-old mature specimen of the new cultivar displays a height of approximately 20 feet and a width of approximately 12 feet at the base. It is estimated that such specimen could ultimately reach a height of approximately 25 to 30 feet and a width of approximately 15 to 20 feet at the base. The hardiness of the new cultivar has been found to exceed that of typical plants of the species.

The new cultivar well meets the needs of the horticultural industry and is well suited for growing in the landscape as a distinctive and highly attractive specimen plant. It may also be grown as a screen or hedge and does well in full sun. The attractive red berries are highly visible and provide nicely contrasting coloration to the green leaves in the landscape.

Asexual propagation of the new cultivar by the use of terminal semi-hardwood cuttings taken during July has been carried out at West Grove, Pa., U.S.A. Such propagation has confirmed that the unique combination of characteristics of the new cultivar is stably established and is consistently transmitted to successive generations.

The new cultivar of the present invention has been named 'Conayule' and is being marketed under the YULE BRITE trademark.

BRIEF DESCRIPTION OF THE PHOTOGRAPHS

The accompanying photographs show as nearly true as is reasonably possible to make the same in color illustrations of this character, a typical specimen of the new cultivar. The illustrated plant was approximately 30 years of age and was growing on its own roots in a grassy area with no supplemental irrigation and no fertilization at West Grove, Pa., U.S.A. The photographs were taken during October, 2003. In FIGS. 2 to 6 dimensions in centimeters are provided at the bottom of the photographs.

FIG. 2 illustrates a typical specimen of a vegetative branch.

FIG. 3 illustrates typical specimens of leaves as viewed from above.

FIG. 4 illustrates typical specimens of leaves as viewed from below.

FIG. 5 illustrates a typical specimen of a flowering branch.

FIG. 6 illustrates a typical specimen of a fruiting branch.

FIG. 7 illustrates a closer view of typical fruit specimens as borne in a cluster at the left and individually presented at the right.

DETAILED DESCRIPTION

Figure 1:
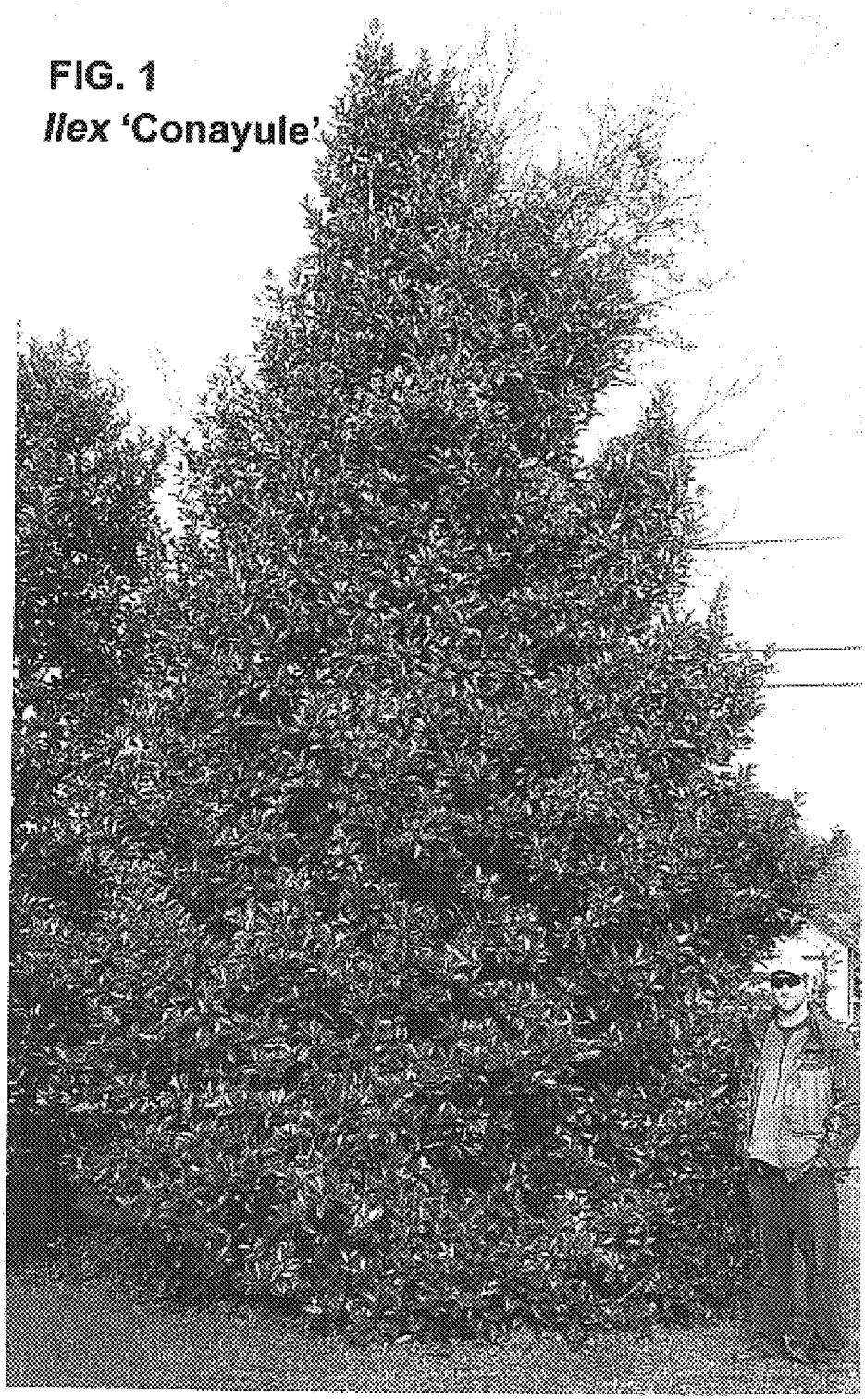
FIG. 1 illustrates the upright moderately narrow pyramidal growth habit of a mature plant of the new cultivar. An adult of typical height is included at the lower right of the photograph in order to provide the viewer a better appreciation of the height of the illustrated plant.

The following is a detailed description of the new cultivar while observing a 30 year-old plant growing on its own roots in the ground in full sun at West Grove, Pa., U.S.A. Color terminology is in accordance with The R.H.S. Colour Chart (1989 Edition) of The Royal Horticultural Society, London, England, except where general color terms of ordinary dictionary significance are used.

Type: Hardy broad-leaved evergreen tree for garden decoration and general landscape use.

Parentage: *Ilex aquifolium*×*Ilex latifolia*.

Plant:

- *Growth habit.*—Upright moderately narrow pyramid.
- *Height.*—Approximately 20 feet (approximately 6.1 meters).
- *Width.*—Approximately 12 feet (approximately 3.6 meters) at the base.

Stems:

- *Texture.*—Smooth and glabrous.
- *Color.*—Near Yellow-Green Group 146A, 146B, 146C, and 147B on current season's growth.
- *Length.*—On the lower one-half of the tree the current season's growth commonly measures approximately 10 to 35 cm in length with an average length of approximately 21 cm.
- *Diameter.*—Approximately 12 mm.
- *Internode length.*—Approximately 1.25 cm.

Leaves:

- *Blade length.*—Commonly approximately 5 to 11.5 cm with an average of approximately 9 cm.
- *Blade width.*—Commonly approximately 2 to nearly 7 cm with an average of approximately 4.7 cm. The overall leaf size varies with the availability of water and fertilization. Accordingly, leaf sizes outside the above ranges are possible.
- *Shape.*—Typically narrowly elliptical to elliptical to narrowly ovate to broadly ovate to occasionally oblong lanceolate and often with a distinct keeled appearance.
- *Margin.*—Typically repand (undulate) to occasionally sinuate, and dentate-spiny with stiff sharp tips on the teeth (as illustrated).
- *Apex.*—Typically narrowly to medium acute-mucronate.
- *Base.*—Obtuse to rounded to nearly cuneate.
- *Texture.*—Surface texture is glabrous, and the physical texture is coriaceous (leathery) and very stiff.
- *Color.*—The upper surface is a very rich deep dark shiny green approaching Green Group 139A with some shading towards Yellow-Green Group 147A with a midrib near Yellow-Group 144A shading to Yellow-Green Group 144B, and the lower surface possesses a matte surface near Yellow-Green Group 146B and 146C with a midrib near Yellow-Green Group 144B and 144C.

Petioles:

- *Length.*—Commonly approximately 11 to 22 mm with an average of approximately 16 mm.
- *Diameter.*—Commonly approximately 1.9 to 2.9 mm with an average of approximately 2.6 mm.
- *Texture.*—Smooth and glabrous.
- *Color.*—Near Yellow-Green Group 144B, 144C and 145A with some anthocyanin pigmentation near Greyed-Purple Group 184C.

Inflorescence:

- *Type.*—Fasciculate, axillary, and dioecious borne on old wood. The plant is unisexual and female functional only.
- *Bearing.*—In clusters numbering approximately 7 to 15 per cluster, and commonly approximately 8 to 10 flowers per cluster.
- *Buds.*—Substantially globose in shape, approximately 8 mm in length, approximately 7 mm in width, and Yellow-Green Group 144B in coloration.
- *Petal count.*—Four.
- *Petal shape.*—Ovate.
- *Petal apex.*—Broadly obtuse-rounded.
- *Petal base.*—Truncate.
- *Petal length.*—Approximately 3.7 to 4.5 mm with an average of approximately 4 mm.
- *Petal width.*—Approximately 2.9 to 3.8 mm with an average of approximately 3.2 mm.
- *Petal margin.*—Entire.
- *Flower size.*—Approximately 7 to 8.5 mm in diameter when fully open.
- *Flower color.*—The petals display a greenish-white overall appearance. The upper petal surface commonly is near Green-White Group 157A with some shading through Green-White Group 157B, 157C and 157D, and the lower petal surface commonly is near Green-White Group 157A with some shading through Green-White Group 157B, 157C and 157D as well as Yellow-Green Group 145C and 145D thereby imparting a more yellowish-green appearance than is present on the upper petal surface.
- *Sepals.*—Absent.
- *Pedicel length.*—Commonly ranges from 8 to 11 mm.
- *Pedicel diameter.*—Commonly ranges from 0.9 to 1.1 mm.
- *Pedicel color.*—Yellow-Green Group 144B.
- *Blood period.*—Commonly mid- to late-May to early June in Southeast Pennsylvania, U.S.A.
- *Fragrance.*—None observed.

Fruit:

*General appearance.*—A red drupe (berry) typically containing 4 seeds (pyrenes).

*Shape.*—Typically obovoid or pyriform to nearly subglobose to rarely globose with a flattened apex.

*Length.*—Commonly ranges from approximately 8 to 10 mm with an average of approximately 9 mm.

*Number.*—The number of drupes commonly ranges from approximately 2 to 15 with an average of approximately 8.

*Color.*—When mature near Red Group 46A lightening to near Red Group 45A commonly with significant coloration of Red Group 44A, 44B, 45B and 46B.

*Seed number.*—Typically 4 pyrenes per fruit.

*Seed length.*—Typically approximately 5.5 to 7 mm with an average of approximately 6 mm.

*Seed diameter.*—Typically approximately 2.6 to 3.7 mm with an average of approximately 3 mm.

*Seed surface texture.*—Typically highly pitted and grooved and irregularly ribbed.

*Seed color.*—Ridges typically are near Orange-White Group 159A and 159B and Greyed-Orange Group 164D to 165D and the pitted areas typically are near Greyed-Orange Group 165B and 165C.

Development:

*Hardiness.*—Generally more hardy than typical plants of the species. Is satisfactorily grown in U.S.D.A. Hardiness Zone 6b and has withstood temperatures of −10° F.

*Disease tolerance.*—No specific susceptibility to common *Ilex* diseases has been observed to date under commercial growing conditions and in unsprayed areas.

*Insect tolerance.*—No specific susceptibility to *Ilex* pests has been observed to date under commercial growing conditions and in unsprayed areas.

*Drought tolerance.*—Good.

Plants of the new 'Conayule' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Ilex×koehneana* plant having the following combination of characteristics:

(a) displays a moderate to fast growing upright moderately narrow pyramidal growth habit, (b) forms in abundance showy red fruit that commonly is retained on the plant well into February, (c) displays improved cold hardiness, and (d) displays good drought tolerance in established plantings;

substantially as shown and described.

* * * * *

*Ilex* 'Conayule'

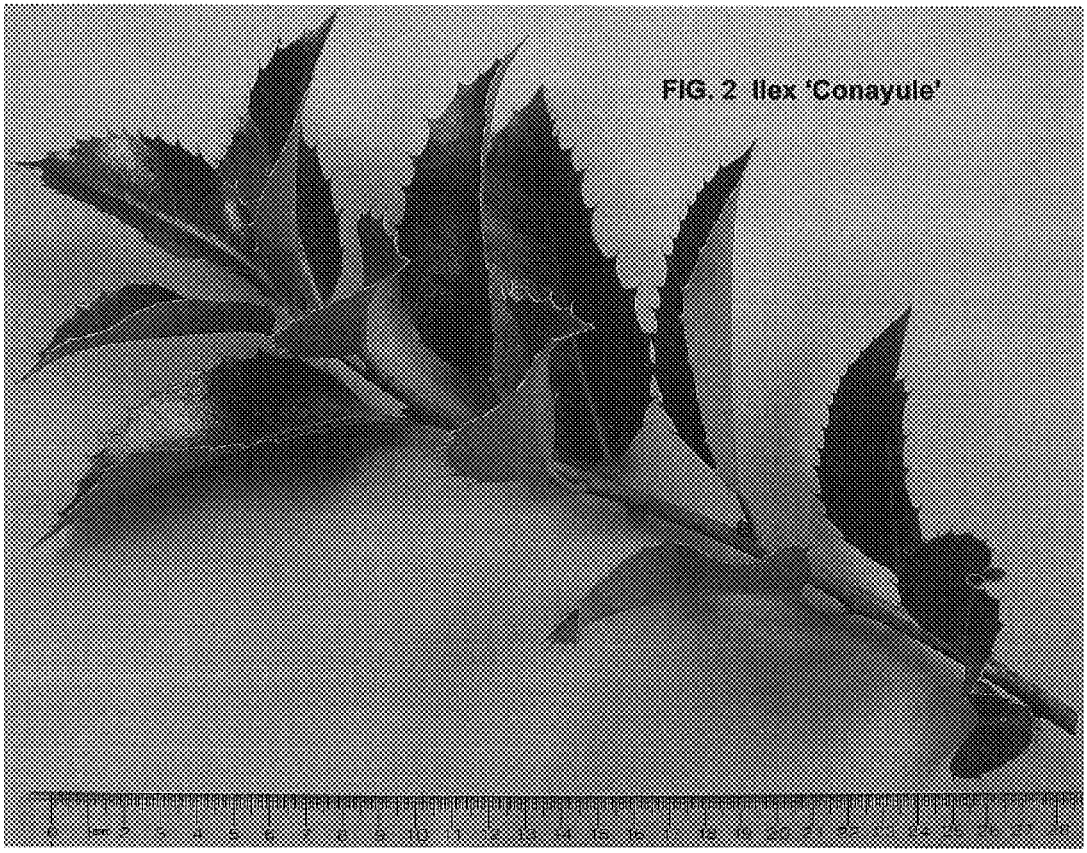
FIG. 2 Ilex 'Conayule'

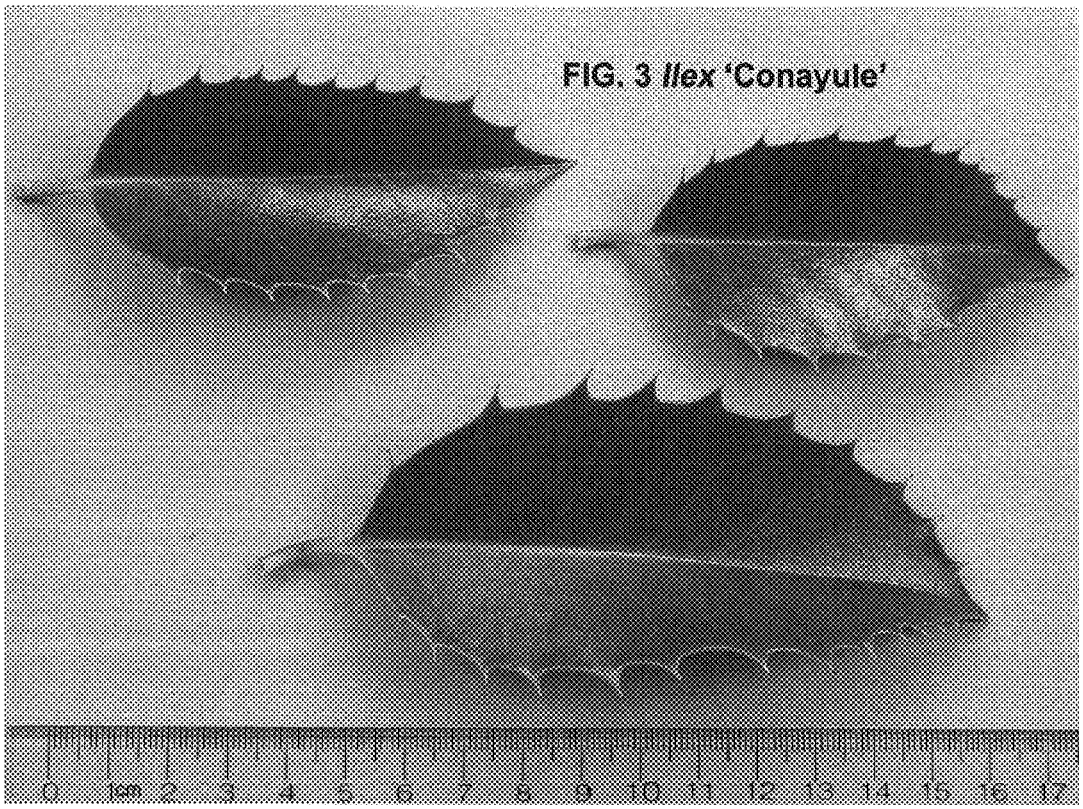
FIG. 3 *Ilex* 'Conayule'

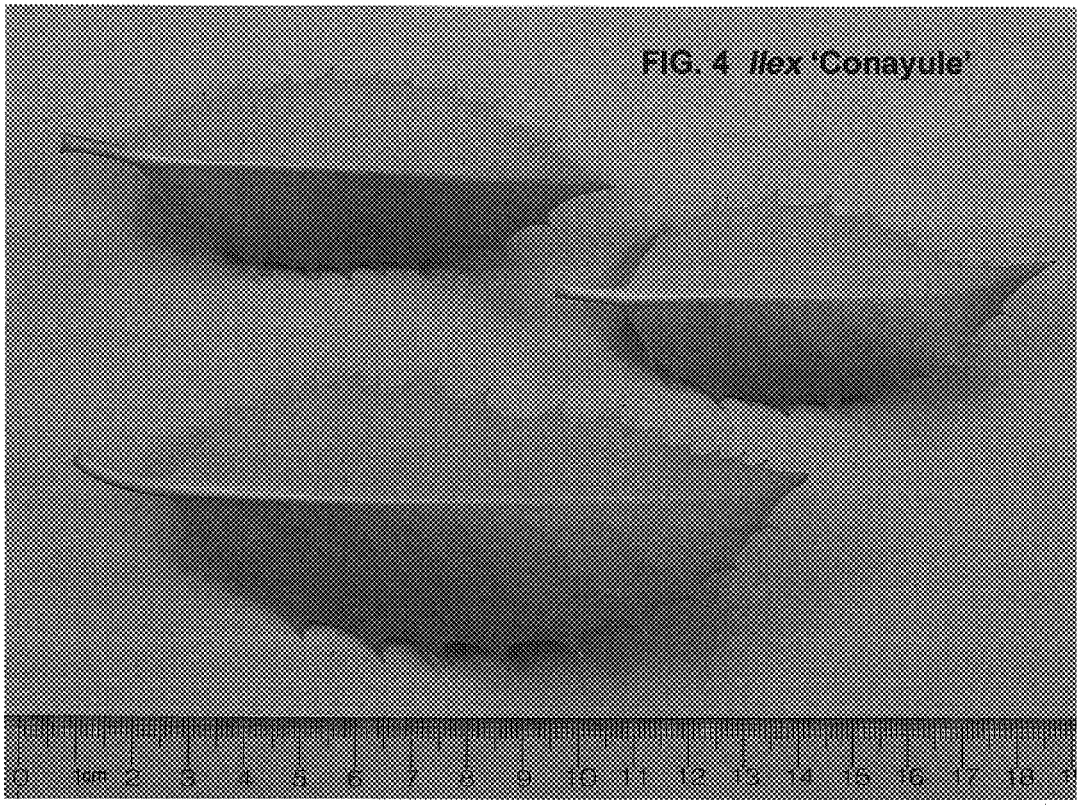
FIG. 4 *Ilex* 'Conayule'

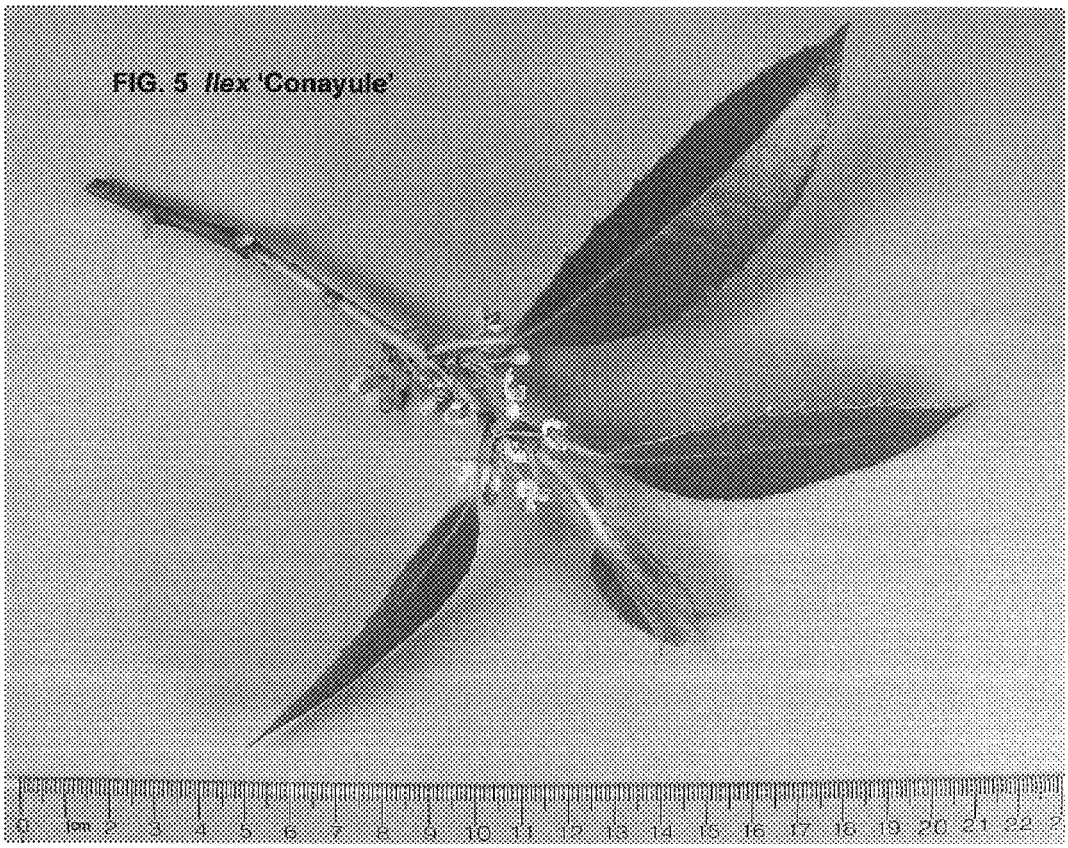
FIG. 5 *Ilex* 'Conayule'

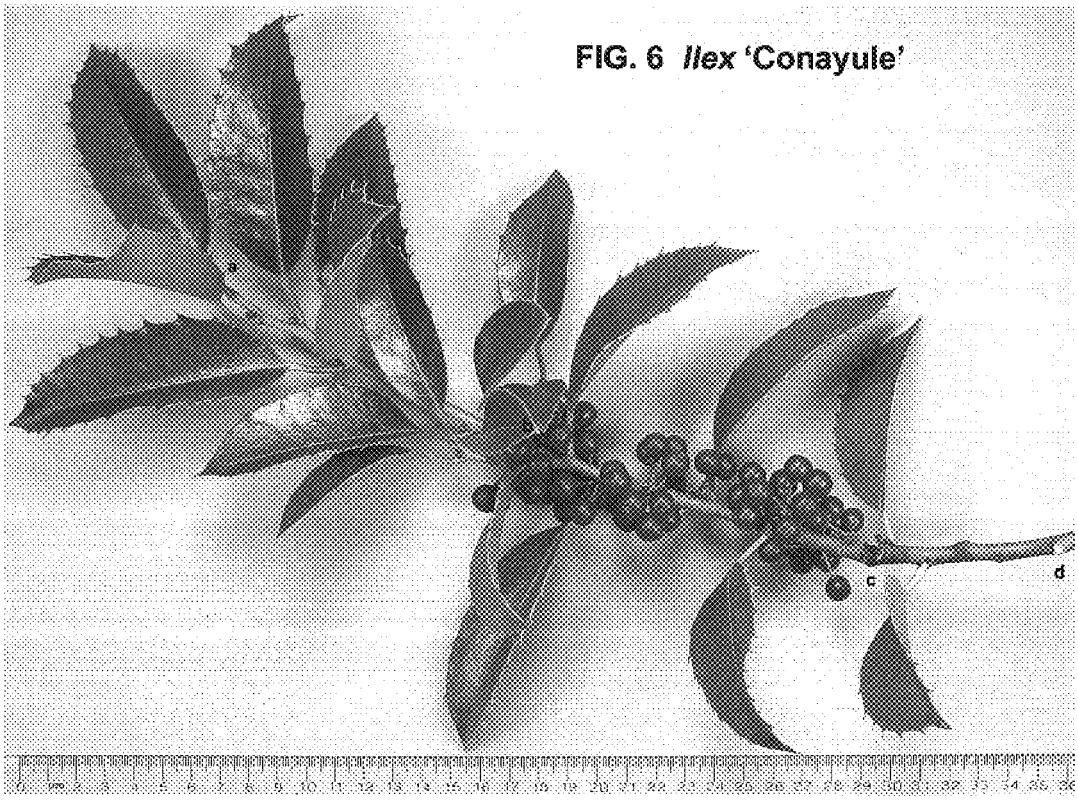
FIG. 6 *Ilex* 'Conayule'

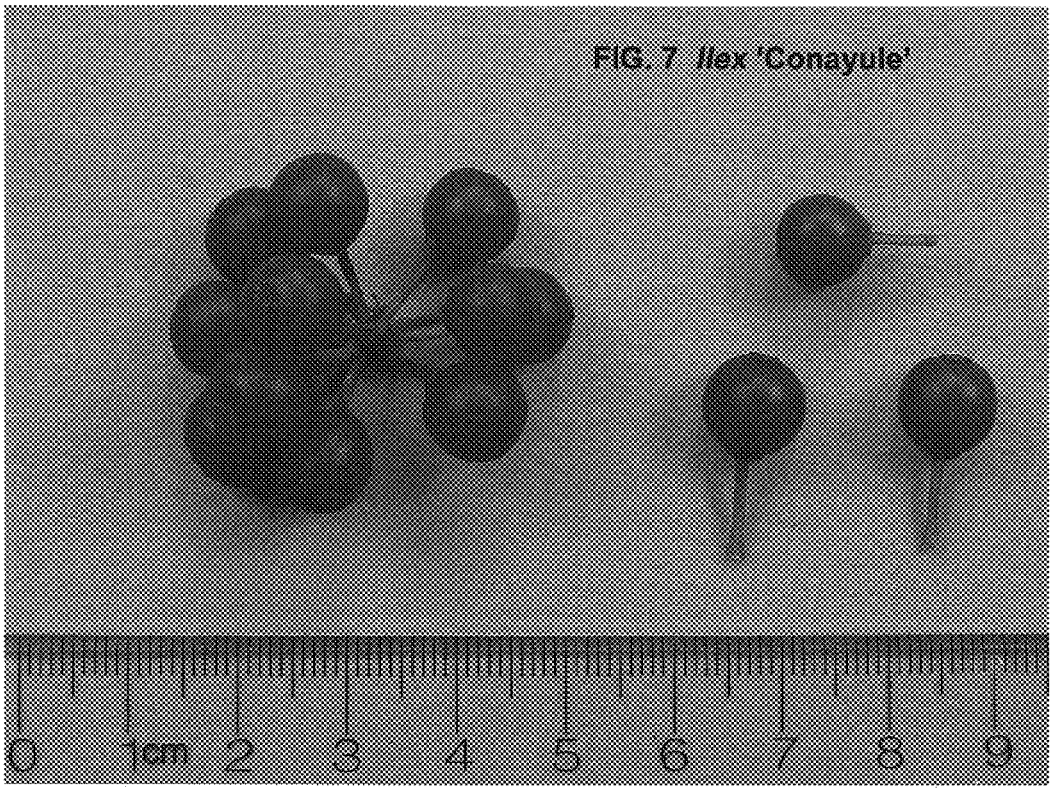
FIG. 7 *Ilex* 'Conayule'